US011970604B2

(12) United States Patent
Meng et al.

(10) Patent No.: US 11,970,604 B2
(45) Date of Patent: Apr. 30, 2024

(54) GERM-REPELLENT PLASTIC, A GAS PATHWAY OF A RESPIRATORY DEVICE CONTAINING, AND A MANUFACTURING METHOD THEREFOR

(71) Applicant: VINCENT MEDICAL MANUFACTURING CO., LTD., Hong Kong (CN)

(72) Inventors: Wenjun Meng, Hong Kong (CN); Sau Kuen Connie Kwok, Hong Kong (CN); Yueying Chen, Hong Kong (CN); Mingyu Zhang, Hong Kong (CN); Kwok Fu Fu, Hong Kong (CN); Ching Sau Chu, Hong Kong (CN)

(73) Assignee: VINCENT MEDICAL MANUFACTURING CO., LTD., Hong Kong (CN)

( * ) Notice: Subject to any disclaimer, the term of this patent is extended or adjusted under 35 U.S.C. 154(b) by 882 days.

(21) Appl. No.: 17/044,512

(22) PCT Filed: Apr. 9, 2018

(86) PCT No.: PCT/CN2018/082327
§ 371 (c)(1),
(2) Date: Oct. 1, 2020

(87) PCT Pub. No.: WO2019/195981
PCT Pub. Date: Oct. 17, 2019

(65) Prior Publication Data
US 2021/0038854 A1 Feb. 11, 2021

(51) Int. Cl.
*C08L 27/06* (2006.01)
*C08K 5/04* (2006.01)
*A61M 16/08* (2006.01)
*C08L 23/06* (2006.01)
*C08L 23/08* (2006.01)
*C08L 23/12* (2006.01)
*C08L 71/02* (2006.01)

(52) U.S. Cl.
CPC ............... *C08L 27/06* (2013.01); *C08K 5/04* (2013.01); *A61M 16/0875* (2013.01); *A61M 2205/0205* (2013.01); *C08L 23/06* (2013.01); *C08L 23/0853* (2013.01); *C08L 23/12* (2013.01); *C08L 71/02* (2013.01); *C08L 2205/025* (2013.01); *C08L 2205/035* (2013.01); *C08L 2310/00* (2013.01)

(58) Field of Classification Search
CPC ...... C08L 27/06; C08L 71/02; C08L 23/0869; C08L 23/0853; C08L 23/0815; C08L 23/06; C08L 23/12
See application file for complete search history.

(56) References Cited

U.S. PATENT DOCUMENTS

| 4,222,913 A | 9/1980 | Cooper |
| 2012/0022188 A1* | 1/2012 | Changping ......... C08L 23/0815 |
| | | 524/52 |

FOREIGN PATENT DOCUMENTS

| CN | 102131855 | 7/2011 |
| CN | 104403170 | 3/2015 |
| CN | 104829969 A | 8/2015 |
| CN | 104945790 | 9/2015 |
| CN | 105664320 | 6/2016 |
| CN | 106009396 | 10/2016 |
| CN | 106188968 A | 12/2016 |
| CN | 106715568 | 5/2017 |
| CN | 106750995 | 5/2017 |
| CN | 107461867 | 12/2017 |
| CN | 107674339 A | 2/2018 |
| CN | 107793743 | 3/2018 |
| EP | 0074237 | 4/1985 |
| EP | 1464677 A2 | 10/2004 |
| GB | 0944383 A | 12/1963 |
| KR | 2009-0089143 | 8/2009 |

(Continued)

OTHER PUBLICATIONS

Chinese First Office Action for Chinese Application No. 201880094203.8, dated Aug. 22, 2022, 17 pages with translation.
Supplementary European Search Report, Mar. 10, 2022, 16.
Tan K et al., "Preparation and characterization of thermoplastic elastomer of poly(vinyl chloride) and chlorinated waste rubber", Polymer Testing, Elsevier, Amsterdam, NL, vol. 28, No. 1, Feb. 1, 2009 (Feb. 1, 2009), pp. 2-7, XP025768211.
European Search Report issued in PCT/CN2018082327 dated Oct. 22, 2021.
International Search Report cited in PCT/CN2018/082327 mailed Jan. 17, 2019.

*Primary Examiner* — Peter A Salamon
(74) *Attorney, Agent, or Firm* — Workman Nydegger

(57) ABSTRACT

A germ-repellent plastic for use in a gas pathway of a respiratory device contains an anti-biofouling compound, and a basic plastic. The anti-biofouling compound is optionally selected from the group of a polyol, a polyether polyol, a polyol derivative, and a combination thereof; or the anti-biofouling compound is selected from the group consisting of a polyether, a poly(ethylene glycol) ether, a polysorbate, and a combination thereof; or the anti-biofouling compound is selected from the group consisting of poly(ethylene glycol) sorbitan monolaurate, poly(ethylene glycol) sorbitan monooleate, poly(ethylene glycol) sorbitol hexaoleate, ceteareth, and a combination thereof. The basic plastic is selected from the group of a blend of a low-density polyethylene polymer and an ethyl vinyl acetate copolymer, a blend of a polypropylene polymer and an ethyl vinyl acetate copolymer, a blend of polyolefin elastomer polymers and a polyvinyl chloride polymer. A method for manufacturing such a germ-repellent plastic, a gas pathway component of a respiratory device containing the germ-repellent plastic, and a respiratory device are also described.

16 Claims, 2 Drawing Sheets

(56) References Cited

FOREIGN PATENT DOCUMENTS

| KR | 20090089143 | 8/2009 |
|---|---|---|
| WO | WO2017204806 | 11/2017 |

\* cited by examiner

GERM-REPELLENT PLASTIC, A GAS PATHWAY OF A RESPIRATORY DEVICE CONTAINING, AND A MANUFACTURING METHOD THEREFOR

FIELD OF THE INVENTION

The present invention relates to a plastic, a method for manufacturing a plastic, and a gas pathway of a respiratory device, and a respiratory device containing a plastic.

BACKGROUND

Medical breathing devices, especially the breathing tube components, formed from plastics may be manufactured by a variety of methods, such as extrusion, especially in the case of tubes, injection moulding, vacuum forming, etc. as desired.

Anti-bacterial and/or anti-microbial plastics exist which contain bacteria-killing and microbe-killing materials either embedded into the plastic, and/or coated thereupon. These plastics seek to kill any bacteria, microbes, etc. that touch the plastic, so as to reduce the chance of infection, transmission, etc. However, it has been found that such anti-bacterial and/or anti-microbial plastics may be difficult to register for use in medical devices, as the regulations concerning anti-bacterial and/or anti-microbial materials varies greatly from country-to-country. Additional concerns relate to how long the anti-bacterial and/or anti-microbial effect will last, leaching of the active material, e.g. nano silver particles and ions may be harmful and dangerous to humans, the effect of solvents or other materials on the active material, etc. Furthermore, there is growing concern about the overuse of antibiotics which can lead to an increase of resistant and multi-resistant organisms.

There are many patents and publications related to coatings or release of the antimicrobials which make the surface germ-repellent. "Antifouling Coatings: Recent Developments in the Design of Surfaces That Prevent Fouling by Proteins, Bacteria, and Marine Organisms", Bannerjee, et al., Adv. Mater., vol. 23, 690-718 (Wiley, 2011); US 2005/0008671 A1 to Antwerp, published on 13 Jan. 2005; US 2009/0155335 A1 to O'Shaughnessey, et al., published on 18 Jun. 2009 and assigned to Pabst Patent Group LLP; CN 104847971 A assigned to Anhui Meiting Special Electric Cable Materials Co., Ltd., published on 19 Aug. 2015, and CN 1242781 A to Tanahashi, published on 26 Jan. 2000, and assigned to Toray Industries. However, previous technologies may cause problems such as, for example, merely form a coating on the basic plastic, may easily leach out of the basic plastic.

Other technologies graft a polymer on to a plastic, typically on a side-chain, such as, for example, US 2011/0305898 A1 to Zhang, et al., published on 15 Dec. 2011; US 2011/0124772 A1 to Wang, et al., published on 26 May 2011.

Another existing category of plastics is germ-repellent plastics, which typically contain an anti-biofouling compound which may, for example, provide a surface from which bacteria, microbes, etc. easily slide off of. The object of these materials is often to create a surface which reduces the chance of bacterial attachment thereto, which in turn reduces the chances of colony growth, the formation of biofilms, etc. These germ-repellent plastics contain a germ-repellent material that may be, for example, comingled with an intermediate plastic into a masterbatch, and then comingled with the basic plastic. This is a unique built-in germ-repellent feature to plastics. See, for example, US 2017/0129139 A1 to Lau, et all., published on 11 May 2017, and assigned to Nano and Advanced Materials Institute, Ltd., of Hong Kong. However, this technology may require the identical or substantially identical backbone as the basic plastic, etc.

However, it has been found that medical breathing devices such as breathing tubes and breathing apparatuses, are especially prone to bacterial and microbial contamination, the formation of biofilms, etc. as the air therein may often be warm, humid and/or high in $O_2$. In addition, it has been found that gases from ventilators or patients may contains infectious microbes which may in turn spread and/or contaminate other areas, surfaces, patients, etc. Furthermore, existing germ-repellent plastics may possess technical limitations such as requiring that the masterbatch contains the same base polymer backbone as the basic plastics. It has been found that technical limitations such as these described may reduce the design flexibility of the medical breathing device manufacturer. In addition, this may cause the cost of the masterbatch and/or the final item to increase.

In addition, the need exists for germ-repellent plastics that may be used with a greater variety of other plastics. Accordingly, the need exists for additional germ-repellent plastics, medical breathing devices made therefrom, and methods of manufacturing such medical breathing devices.

SUMMARY OF THE INVENTION

An embodiment of the present invention relates to a germ-repellent plastic for use in a gas pathway of a respiratory device containing an anti-biofouling compound, and a basic plastic. The anti-biofouling compound is optionally selected from the group of a polyol, a polyether polyol, a polyol derivative, and a combination thereof; or the anti-biofouling compound is selected from the group consisting of a polyether, a poly(ethylene glycol) ether, a polysorbate, and a combination thereof; or the anti-biofouling compound is selected from the group consisting of poly(ethylene glycol) sorbitan monolaurate, poly(ethylene glycol) sorbitan monooleate, poly(ethylene glycol) sorbitol hexaoleate, ceteareth, and a combination thereof. The basic plastic is selected from the group of a blend of a low-density polyethylene polymer and an ethyl vinyl acetate copolymer, a blend of a polypropylene polymer and an ethyl vinyl acetate copolymer, a blend of polyolefin elastomer polymers and a polyvinyl chloride polymer.

An embodiment of the present invention relates to a method for manufacturing a germ-repellent plastic herein, wherein the basic plastic and the anti-biofouling compound are commingled in an extruder.

An embodiment of the present invention relates to a method for manufacturing a germ-repellent plastic for use in a gas pathway of a respiratory device having the steps of providing an anti-biofouling compound, providing a basic plastic, and comingling the anti-biofouling compound with the basic plastic. The anti-biofouling compound is optionally selected from the group of a polyol, a polyether polyol, a polyol derivative, and a combination thereof; or the anti-biofouling compound is selected from the group consisting of a polyether, a poly(ethylene glycol) ether, a polysorbate, and a combination thereof; or the anti-biofouling compound is selected from the group consisting of polyethylene glycol sorbitan monolaurate, poly(ethylene glycol) sorbitan monooleate, poly(ethylene glycol) sorbitol hexaoleate, ceteareth, and a combination thereof. The basic plastic is selected from the group of a blend of a low-density polyethylene polymer and an ethyl vinyl acetate copolymer, a blend of a polypropylene polymer and an ethyl vinyl acetate copolymer, a blend of polyolefin elastomer polymers and a polyvinyl chloride polymer.

An embodiment of the present invention relates to a gas pathway component of a respiratory device containing the germ-repellent plastic herein, or a plastic manufactured according to the method described herein.

An embodiment of the present invention relates to a respiratory device comprising the gas pathway component of a respiratory device herein.

Without intending to be limited by theory, it is believed that the invention herein provides a germ-repellent plastic where the germ-repellency is permanently integrated into the plastic, as opposed to merely coated thereupon. Therefore, the present invention may maintain the germ-repellency benefit for a long time, even, for example, three years of regular room-temperature storage. It is believed that the physical comingling and therefore integration of the anti-biofouling compound with the basic plastic reduces leaching of the anti-biofouling compound form the germ-repellent plastic. It is also believed that the germ-repellent plastic herein may provide a significant reduction in the adhesion of both gram positive bacteria as well as gram-negative bacteria to the germ-repellent plastic herein, as compared to the basic plastic itself.

Without intending to be limited by theory, it is believed that even in the case of a gas pathway component of a respiratory device formed with the germ-repellent plastic herein provides a reduced chance of biofilm formation, cross-contamination, and/or germ adhesion as compared to the basic plastic itself. It is also believed that the germ-repellent plastic herein may provide the manufacturer with significantly greater design flexibility, as it has been discovered that in some embodiments only one polymeric segment in a masterbatch need be compatible with the basic plastic. In fact, it has been found that in some embodiments, no masterbatch is needed at all, thereby saving by reducing the number/amount of raw materials, manufacturing complexity and/or expense.

DESCRIPTION OF THE PREFERRED EMBODIMENTS

Figure 1:
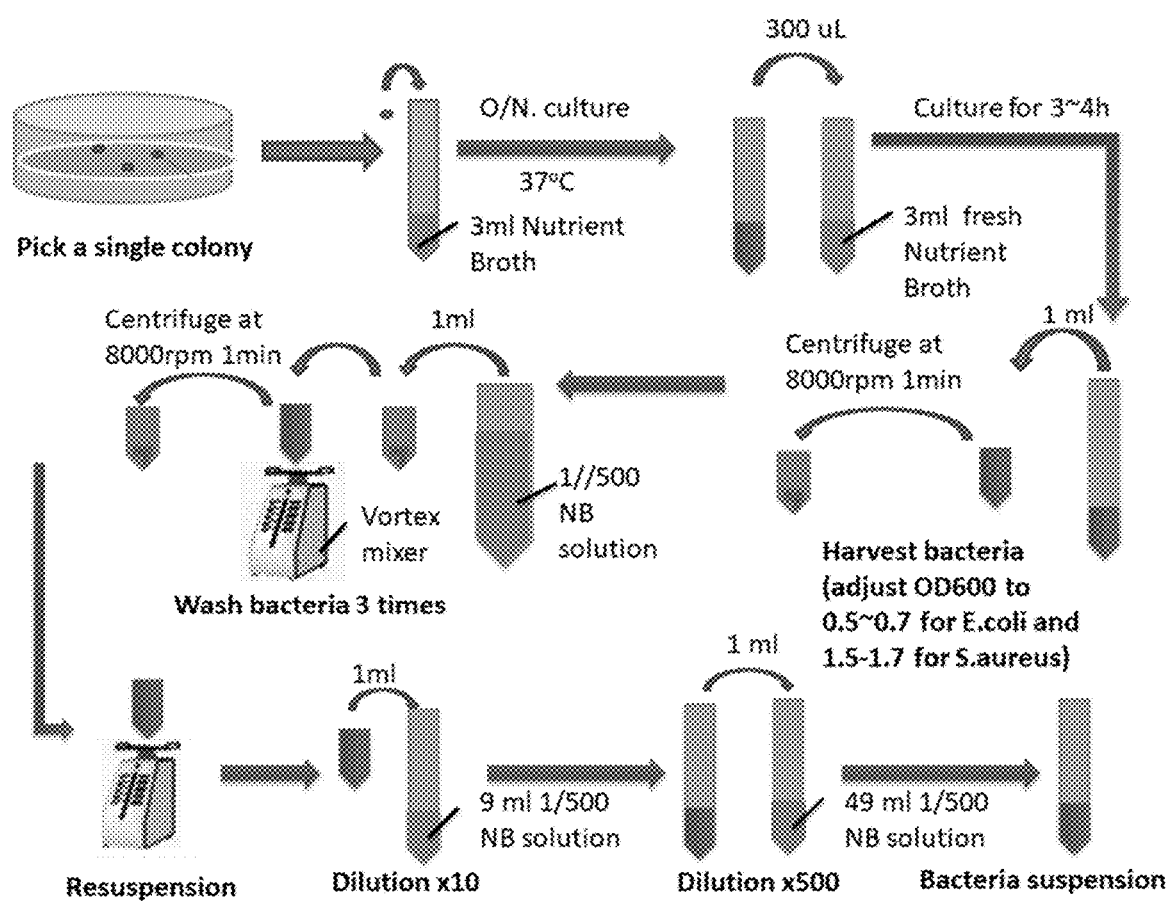
FIG. 1 is a flowchart illustrating the procedure of preparation of test inoculum of bacteria.

Unless otherwise specifically provided, all tests herein are conducted at standard conditions which include a room and testing temperature of 25° C., sea level (1 atm.) pressure, pH 7, and all measurements are made in metric units. Furthermore, all percentages, ratios, etc. herein are by weight of the final product, material, plastic, etc. as appropriate, unless specifically indicated otherwise.

As used herein, the term "comingling" and its other forms such as "comingled", etc. indicates that at least two materials are physically mixed together; or physically mixed together and chemically mixed together; or physically mixed together and chemically bonded together.

As used herein, the term "germ" indicates a microbe; or bacteria.

As used herein, the term "germ-repellent" when describing a material (or plastic, etc.) and its other grammatical forms, such as "germ-repellency", etc. indicate that the material reduces the physical adhesion; or the initial physical adhesion, of microbes, bacteria, etc. to the material (or plastic, etc.) and/or enhances the likelihood that they become physically dislodged from the plastic material.

An embodiment of the present invention relates to a germ-repellent plastic containing an anti-biofouling compound and a basic plastic. The anti-biofouling compound is optionally selected from the group of a polyol, a polyether polyol, a polyol derivative, and a combination thereof; or wherein the anti-biofouling compound is selected from the group consisting of a polyether, a poly(ethylene glycol) ether, a polysorbate, and a combination thereof; or the anti-biofouling compound is selected from the group consisting of poly(ethylene glycol) sorbitan monolaurate, poly(ethylene glycol) (PEG) sorbitan monooleate, poly(ethylene glycol) (PEG) sorbitol hexaoleate, ceteareth, and a combination thereof. The basic plastic is selected from the group of a blend of a low-density polyethylene (LDPE) polymer and an ethyl vinyl acetate (EVA) copolymer, a blend of a polypropylene (PP) polymer and an EVA copolymer, a blend of polyolefin elastomer (POE) polymers and a polyvinyl chloride (PVC) polymer.

The anti-biofouling compound herein reduces the chance of adhesion of a germ, such as a microbe or bacteria, to adhere to the basic plastic and/or a breathing gas pathway component made from the basic plastic. Without intending to be limited by theory, it is believed that the anti-biofouling compound may, for example, provide a surface from which a biofouling agent (e.g., bacteria, microbes, etc.) may easily slide off of as described herein. The anti-biofouling compound may, for example make the plastic surface very hydrophilic so that there is a thin layer of water on the plastic which prevents the biofouling agent from attaching to the plastic.

The anti-biofouling compounds herein are available from a variety of vendors worldwide in various grades.

In an embodiment herein, the polyol derivative, or polyether polyol is a PEG molecule with from about 1 to about 20 $C_{4-28}$ ester moieties attached thereto.

Ceteareth (e.g., Ceteareth-20, CAS No. 68439-49-6) is a polyglycol ether non-ionic surfactant with the structure:

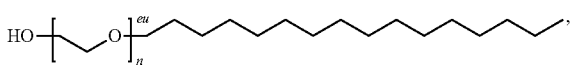

where n indicates the number of ethyl ether repeating units. The ceteareth useful herein has a n from about 2 to about 100; or from about 10 to about 90; or is 20, 40, 60, or 80.

Tween is useful herein, especially Tween 20 and Tween 80. Tween 20 (CAS No. 9005-64-5) is a poly(ethylene glycol) sorbitan monooleate with the structure:

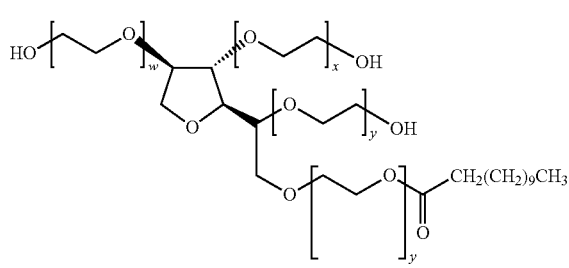

where the sum of w+x+y+z=20.

Tween 80 (CAS No. 9005-65-6) is a poly(ethylene glycol) sorbitan monolaurate with the structure:

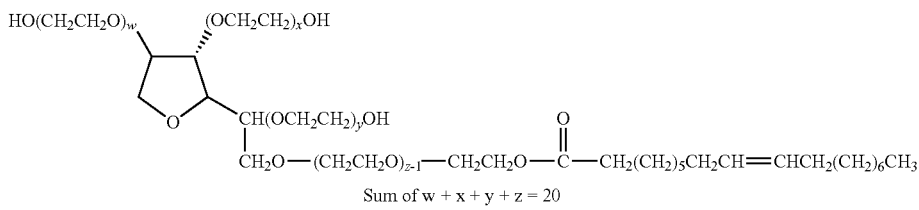

Sum of w + x + y + z = 20 where the sum of w+x+y+z=20.

Poly(ethylene glycol) sorbitol hexaoleate (e.g., CAS No. 57171-56-9) has the structure:

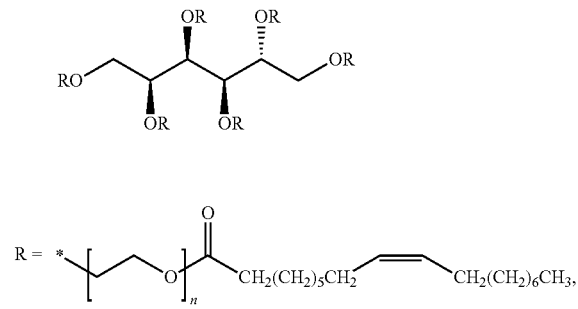

wherein n is a natural number form about 2 to about 100.

In an embodiment herein, the anti-biofouling compound is from about 0.001% by weight to about 50% by weight; or from about 0.001% by weight to about 20% by weight; or from about 0.01% by weight to about 15% by weight, of the germ-repellent plastic.

The basic plastic herein is selected from a blend of a LDPE polymer and an EVA copolymer, a blend of a PP polymer and an EVA copolymer, a blend of POE polymers, and a PVC polymer. In an embodiment herein, the POE useful herein contains a combination of linear alpha-olefin monomers selected from ethylene monomers, 1-butene monomers, 1-hexane monomers, 1-octene monomers, and 1-decene monomers; or ethylene monomers and 1-octene monomers. These basic plastics are available from vendors around the world in a variety of grades and forms.

In an embodiment herein, the basic plastic makes up from about 50% by weight to about 99.999% by weight; or from about 80% by weight to about 99.999% by weight; or from about 85% by weight to about 99.99% by weight, of the germ-repellent plastic.

In an embodiment herein, the anti-biofouling compound is comingled with an intermediate plastic to form a masterbatch. The masterbatch is then comingled with the basic plastic to form the germ-repellent plastic. In an embodiment herein, the intermediate plastic is a random terpolymer; or the random terpolymer contains a monomer selected from the group of an ethylene monomer, an acrylic ester monomer, a maleic anhydride monomer, and a combination thereof; or a random terpolymer comprising an ethylene monomer, an acrylic ester monomer, and a maleic anhydride monomer; or a random terpolymer comprising a polymer backbone comprising ethylene monomers, acrylic ester monomers, and maleic anhydride monomers. Typically, in a random terpolymer, the order of the monomers is randomly-determined by the actual stoichiometry and reaction kinetics of the particular monomers present at the time of polymerisation.

In an embodiment herein, the intermediate plastic contains at least one polymeric segment that is compatible with the basic plastic. However, it is believed that the present invention is significantly different from previous plastics known in the art, in that the intermediate plastic herein need not be exactly the same base polymer backbone as the basic plastic, but in some embodiments need only contain a single common polymeric segment. Without intending to be limited by theory, it is believed that in some embodiments the intermediate does not need to; or does not, contain the same polymeric segment as the basic plastic.

In a preferred embodiment herein the intermediate polymer is not a grafted polymer, in that there are no significant monomer units which branch off from the (essentially linear) polymer backbone. Without intending to be limited by theory, it is believed that in some cases, especially when the basic plastic is a blend of LDPE/EVA, a blend of PP/EVA, and/or a blend of POEs, the intermediate plastic helps to hold and homogenously-distribute the anti-biofouling compound throughout the basic plastic.

In an embodiment herein, the anti-biofouling compound and the intermediate plastic are commingled to form a masterbatch; or the anti-biofouling compound and the intermediate plastic are commingled in an extruder to form a masterbatch; or the anti-biofouling compound and the intermediate plastic are polymerized together to form a masterbatch. Without intending to be limited by theory, it is believed that such a process ensures that the anti-biofouling compound is permanently associated with the basic plastic, which in turn may provide an improved plastic that reduces the chances of the anti-biofouling compound from leaching from the basic plastic, and increases the germ-repellency benefit longevity.

In an embodiment herein, the masterbatch may be from about 0.001% by weight to about 50% by weight; or from about 0.001% by weight to about 20% by weight; or from about 0.01% by weight to about 15% by weight, of the germ-repellent plastic.

In an embodiment herein, the basic plastic may be from about 50% by weight to about 99.999% by weight; or from about 80% by weight to about 99.999% by weight; or from about 85% by weight to about 99.99% by weight, of the germ-repellent plastic.

In an embodiment herein, when a masterbatch is present, then the anti-biofouling compound may be from about 0.01% by weight to about 25% by weight; or from about 0.1% by weight to about 20% by weight; or from about 0.5% by weight to about 15% by weight of the masterbatch.

Alternatively, in an embodiment herein, when the basic plastic is a blend of POEs, a blend of LDPE/EVA, and/or a blend of PP/EVA, then the masterbatch are comingled together at a weight ratio of from about 1000:1 to about 1:1; or from about 75:1 to about 5:1; or from about 60:1 to about 7:1. In an embodiment herein then the basic plastic is a blend of POEs, or a blend of LDPE/EVA, then the basic plastic and the masterbatch are comingled together at a weight ratio of from about 60:1 to about 40:1. In an embodiment herein, the basic plastic is a blend of PP/EVA, then the basic plastic and the masterbatch are comingled together at a weight ratio of from about 50:1 to about 7:1. In such a case, the intermediate plastic is compatible with the basic plastic, meaning that the intermediate plastic comingles homogenously with the basic plastic and does not cause any visible discolorations, or physical flaws.

In another embodiment herein, the basic plastic is PVC, and there is substantially no; or no, intermediate plastic. In such a case, wherein the basic plastic is a polyvinyl chloride polymer, then the anti-biofouling compound and the PVC polymer may be comingled to (directly) form the germ-repellent plastic. It has been surprisingly found that when the anti-biofouling compound according to the present invention is comingled with PVC, no intermediate plastic is needed to help bind the anti-biofouling compound with the PVC prior to forming the germ-repellent plastic. This in turn avoids the need for pre-forming a masterbatch, which may increase efficiency and/or production speed. Without intending to be limited by theory, it is believed that this is due to the filament-like nature of PVC which easily entangles the anti-biofouling compound and easily may homogenously-distribute it therein.

In an embodiment herein, the PVC and the anti-biofouling compound are comingled at a weight ratio of from about 10000:1 to about 20:1; or from about 7500:1 to about 40:1; or from about 3000:1 to about 75:1.

In an embodiment of the present invention, an additive may be present in the germ-repellent plastic, basic plastic, the anti-biofouling compound, the intermediate plastic, and/or the masterbatch. The additive may include, for example, a UV protector (e.g., a UV absorber, a UV blocker, a UV reflector, etc.), a pigment, a plasticiser, a filler, an extender, a coating, a stabilizer, a catalyst, an initiator, a foaming agent, a thickener, a lubricant, an impact modifier, an anti-block, a clarifier, an antistatic agent, a flame retardant, and a combination thereof. Typically, the additive may be present at from about 0.0001% to about 10% by weight of the germ-repellent plastic.

Method of Manufacturing:

In an embodiment herein, a method for manufacturing a germ-repellent plastic includes the steps of providing an anti-biofouling compound, providing a basic plastic, and comingling the anti-biofouling compound with the basic plastic.

Typically the comingling step is a physical mixing; or a physical mixing and a chemical mixing; or a simultaneous physical mixing and chemical mixing; or a physical mixing and/or a chemical bonding of at least two different materials, such as the basic plastic and the anti-biofouling compound; the anti-biofouling compound and the intermediate plastic; the masterbatch and the basic plastic; etc. The comingling step may be conducted when the basic plastic, the anti-biofouling compound, the intermediate plastic, the masterbatch, and/or any additive are melted and/or in a liquid state.

In an embodiment herein, when the basic plastic is; or contains a blend of a low-density polyethylene polymer and an ethyl vinyl acetate copolymer, a blend of a polypropylene polymer and a ethyl vinyl acetate copolymer, a blend of polyolefin elastomer polymers, and/or a combination thereof, then the manufacturing method herein may further contain the steps of: providing an intermediate plastic, comingling the anti-biofouling compound with the intermediate plastic to form a masterbatch, and comingling the masterbatch with the basic plastic to form the germ-repellent plastic.

In an embodiment of the present invention, the anti-biofouling compound and the basic plastic; or the anti-biofouling compound, the intermediate plastic and the basic plastic; or the masterbatch and the basic plastic are comingled to form a germ-repellent plastic. The comingling step herein may occur via a process such as, for example, melting, moulding, injection moulding, vacuum forming, blow moulding, extruding, co-extruding, mixing, and a combination thereof; or extruding, melting, injection moulding, and a combination thereof; or extruding, injection moulding, and a combination thereof; or extrusion, blow moulding, vacuum forming, and a combination thereof. The extruding may occur in a mould, an extruder, or a combination thereof. The extruder may be, for example, a single-screw extruder, a twin-screw extruder, a no-screw extruder, and others known in the art of plastic manufacturing. Without intending to be limited by theory, it is believed that extrusion may ensure adequate mixing of the anti-biofouling compound, intermediate, and/or masterbatch with the basic plastic to form a consistent and relatively homogenous germ-repellent plastic. It is also believed that comingling the anti-biofouling compound and the basic plastic in an extruder allows sufficiently permanent and homogenous comingling such that the anti-biofouling compound will not significantly leach out of the basic plastic during use, storage, etc.

In an embodiment herein when the basic plastic includes polyvinyl chloride, then the anti-biofouling compound may be comingled directly with the basic plastic to form the germ-repellent plastic.

Gas Pathway Component of a Respiratory Device:

The germ-repellent plastic herein may be formed into a gas pathway component of a respiratory device; or a gas pathway component of a respiratory device such as a breathing tube, a heating gas pathway component, a ventilator component, a humidifier component, a gas mask component, an oxygen conserving device component, an oxygen concentrator component, a pump component, a face mask component, a nasal component, a mouth component, a filter component, a water trap component, a gas sampling line component, a Y-piece, a nebulizer component, and a combination thereof; or an inhalatory breathing tube, an exhalatory breathing tube, a humidifier gas pathway component, a humidifier chamber component, a heating gas pathway component, a tracheal tube component, a respiratory monitor component, an oxygen conserving device component, an oxygen concentrator component, and a combination thereof or an inhalatory breathing tube, an exhalatory breathing tube, a humidifier gas pathway component, a heating gas pathway component, a ventilator component, a nebulizer component, and a combination thereof. The gas pathway component of a respiratory device may be a rigid gas pathway component of a respiratory device and/or a flexible gas pathway component of a respiratory device, as desired.

In an embodiment herein, the manufacturing method herein further contains the step of thermoforming the gas pathway component of respiratory device. The thermoforming step may include a process selected from the group of moulding, extruding, injection, compression, and a combination thereof; or moulding, extruding, and a combination thereof. In an embodiment herein, a soft gas pathway component of a respiratory device may be extruded, while a hard gas pathway component of a respiratory device may be formed by, for example, injection moulding.

Respiratory Device:

The gas pathway of a respiratory device herein may further be contained within and/or form a part of a respiratory device. The respiratory device herein may therefore be, for example, an anaesthesia breathing system, a respiratory humidification system, and a ventilation breathing system, which may contain a humidifier, a ventilator, an oxygen concentrator, an oxygen conservator, a nebulizer, a heater, a breathing circuit, a mask, a pump, an adapter, a filter, and a combination thereof.

Test Methods:

Swab Test:

Preparation of Test Inoculum of Bacteria: *E. coli* (ATCC®8739™) and *S. aureus* (ATCC® 6538 PT™).

A test inoculum of bacteria is prepared and enumerated upon incubation according to the Japanese Industrial Standard (JIS Z 2801:2000). With slight modifications, this JIS is used to test for the antibacterial activity and efficacy to bacteria on the surface of the test samples. Refer to FIG. 1 illustrating the procedure in a pictorial format with descriptions as below:

1) A single colony of bacteria is picked from an agar plate (preserved in 4° C. fridge) and transferred to 3 mL Nutrient Broth for overnight culture;
2) Transfer 300 μL of the cultured bacteria into 3 mL of fresh Nutrient Broth and culture for approximately 3-4 hours;
3) Harvest the Bacteria (OD600 must be adjusted to 0.6-0.7 for *E. coli*; 1.5-1.7 for *S. aureus*) by centrifuge at 8000 rpm for 1-2 min;
4) Wash the bacteria three times by 0.9% NaCl aqueous solution and centrifugation;
5) Re-suspend the obtained bacteria in 1/500 nutrient broth solution (1/500 NB refers to the 500× diluted Nutrient Broth with pH adjusted to 6.8-7.2) to prepare a bacterial solution as the test inoculum. Multiple dilution depends on the testing samples. Normally, dilute *E. coli* suspension 10× and dilute the *S. aureus* suspension 500×.

Sample Incubation and Swab Test

Figure 2:
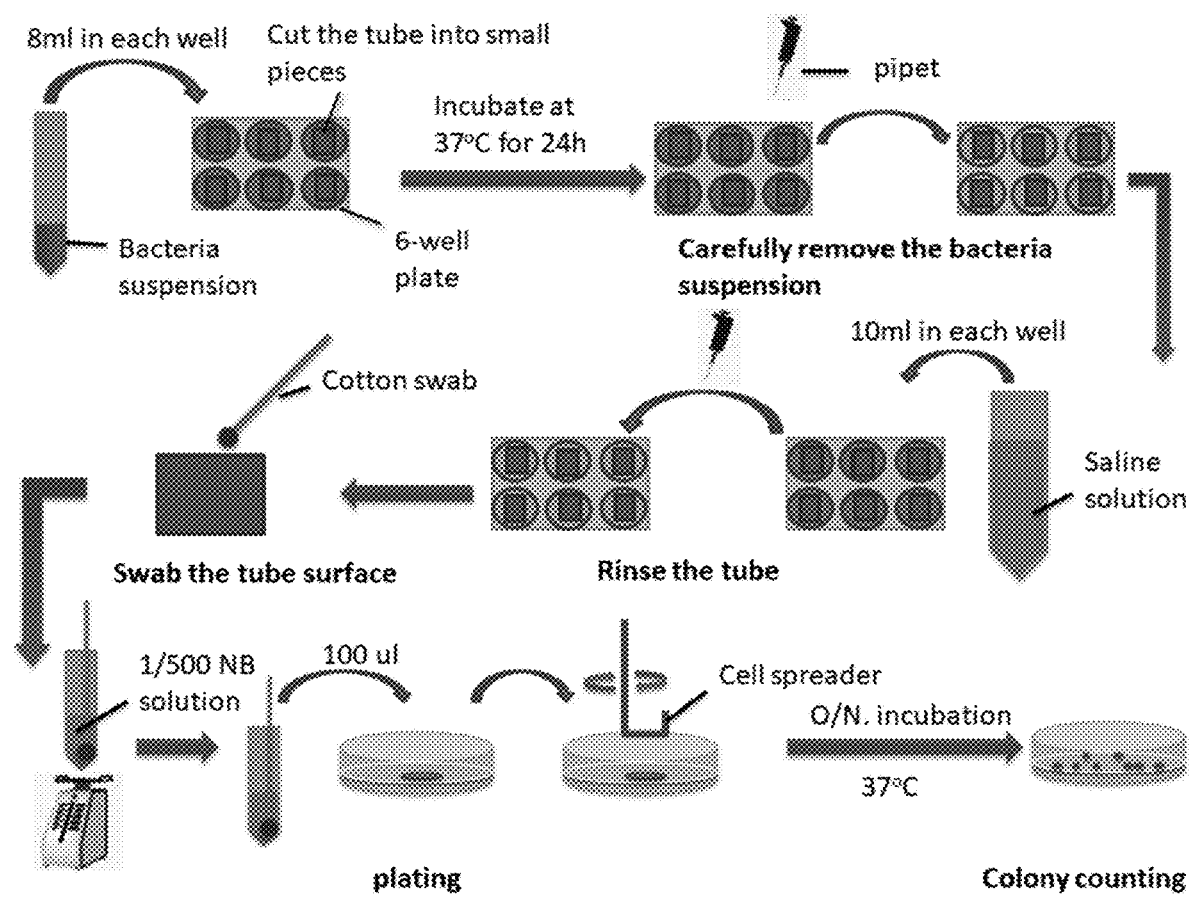
FIG. 2 is a flowchart illustrating the experimental procedure of bioburden challenge and swab test.

After inoculation of the sample with the test inoculum (*E. coli* or *S. aureus*) the samples are incubated at 37° C. for 24 hours. A swab test was used to examine the bacteria attached on the sample surface. The experimental procedure is as follows (c.f., FIG. 2):

1) Cut the sample (e.g. tubes) into small pieces and put them into a sterilized 6-well plate.
2) Transfer 8 mL of as-prepared bacterial suspension into each well and incubate at 37° C. for 24 hours.
3) Carefully remove the bacteria suspension.
4) Rinse with 0.9% NaCl aqueous solution and using the same volume to wash for every sample.
5) Use a sterile cotton or 3M quick swab tips applicator to swab the surface of the sample surface and plate either manually using a cell spreader or more consistently with an automated spiral plater (e.g., Eddy Jet 2, IUL, S.A.).
6) After incubation for overnight or up to 24 hours, count the colonies formed on the agar plates.

Without intending to be limited by theory, it is believed that the use of *E. coli* in the above test is representative of the adhesion of other gram-negative bacteria and that the use of *S. aureus* in the above test is representative of other gram-positive bacteria. Accordingly, it is believed that the results of this test are generally representative of other bacteria.

Based on the above test, and as used herein, the germ reduction percentage is calculated as:

[average # cfu on control plastic−average # cfu on test plastic]*100 [average # cfu on control plastic]

As used herein the term "cfu" indicates bacterial colony forming units.

In an embodiment herein, the germ-repellent plastic possesses a germ-repellent efficiency of at least about 50%; or at least about 75%; or at least about 85%; or at least about 90%; or at least about 95%. In an embodiment herein, the germ-repellent plastic possesses a germ-repellent efficiency for *E. coli* of from at least about 80%; or at least about 85%; or at least about 90%; or at least about 95%. In an embodiment herein, the germ-repellent plastic possesses a germ-repellent efficiency for *S. aureus* of from at least about 60%; or at least about 70%; or at least about 80%; or at least about 85%.

Other rests useful herein include ISO 10993 Biological Evaluation of Medical Devices, and especially its variations ISO 10993-5 and ISO 10993-10; ISO18562 Biocompatibility evaluation of breathing gas pathways in healthcare applications) test, and ASTM F1980-07 Standard Guide for Accelerated Ageing of Sterile Barrier Systems for Medical Devices.

In tests where the germ-repellent plastic sample is subjected to accelerated ageing, then the germ-repellent plastic sample is aged according to ASTM F1980-07. Under the conditions in ASTM F1980-07, accelerated ageing for 97 days is roughly equivalent to 3 years of normal (room temperature) storage. The germ-repellent plastic samples are then tested and compared to control plastic samples (that have not been subject to accelerated ageing) according to the swab test, above, including incubating with the testing bacterial solution for 24 hours.

In an embodiment herein, the germ-repellent plastic possesses a germ-repellent efficiency of at least about 50%; or at least about 75%; or at least about 85%; or at least about 90%; or at least about 95% after greater than or equal to about 7.4 months of storage (or 20 days of accelerated ageing); or after greater than or equal to about 12 months of storage (or 33 days of accelerated ageing); or after greater than or equal to about 1.5 years of storage (or 43 days of accelerated ageing); or after greater than or equal to about 3 years of storage (or 97 days of accelerated ageing).

In other words, the germ-repellent plastic herein, by maintaining a germ-repellent efficiency of at least about 50%; or at least about 75%; or at least about 85%; or at least about 90%; or at least about 95% indicates that it has a shelf life of greater than or equal to about 7.4 months of storage (or 20 days of accelerated ageing); or after greater than or equal to about 12 months of storage (or 33 days of accelerated ageing); or after greater than or equal to about 1.5 years of storage (or 43 days of accelerated ageing); or after greater than or equal to about 3 years of storage (or 97 days of accelerated ageing).

In an embodiment herein, the germ-repellent plastic is biocompatible according to the ISO 10993 test, the ISO 18562 test, and a combination thereof; or is biocompatible according to the ISO 10993-5 test, the ISO 10993-10 test, and the ISO 18562 test.

Additional tests known in the art may be relevant herein, such as, for example, tensile tests, melt flow index tests, thermo characteristics tests, etc. Specifically ASTM D1238-10 to measure a sample's melt flow index, conducted at 190° C. and with a weight of 2.16 kg may be useful herein.

However, one benefit of the germ-repellent plastic herein, is that for such physical properties measured by such tests, the germ-repellent plastic varies very little from the basic plastic. Accordingly, in an embodiment herein, the germ-repellent plastic has a physical property, and the basic plastic has the same physical property. When the germ-repellent plastic's physical property is measured according to an industry-standard test, and when the basic plastic's same physical property is measured by the same industry-standard test, then the germ-repellent plastic's physical property differs from the basic plastic's same physical property by less than or equal to about ±20%; or ±10%; or ±5%.

Example 1

A mixture of 8.3% by weight of an EVA basic plastic, 83.3% by weight ethylene/acrylic acid/maleic acid terpolymer intermediate plastic and 8.3% by weight ceteareth anti-biofouling compound are comingled to form a masterbatch. Specifically, the anti-biofouling compound, EVA basic plastic and the intermediate plastic are comingled together in a twin-screw extruder having a temperature ranging from 90° C. in the front to 190° C. in the rear.

The (main) basic plastic is a blend of two ethylene-octene POEs. The masterbatch is combined with the basic plastic at a weight ratio of 1:54. The masterbatch and the basic plastic are fed into a single-screw extruder having a temperature ranging from 90° C. in the front to 235° C. in the rear to form a germ-repellent plastic (A). The single-screw extruder extrudes the germ-repellent plastic in the form of a sheet.

The weight percentage in the final germ-repellent plastic sheet is therefore: 0.15% EVA basic plastic, 1.5% ethylene/acrylic acid/maleic acid terpolymer intermediate plastic, 0.15% ceteareth anti-biofouling compound, and 98.2% POE blend.

A comparative plastic (Control 1) containing the same blend of two POEs is also prepared in an identical manner, except that that this comparative sample did not contain any masterbatch, intermediate plastic, or anti-biofouling compound.

A swab test (above) is conducted comparing germ-repellency of the germ-repellent plastic (A) with that of the comparative plastic (Control 1).

TABLE 1

EXAMPLE 1,

Sheet Sample with *E. coli*

|  | Replicate 1 | Replicate 2 | Replicate 3 | Average |
|---|---|---|---|---|
| comparative plastic (Control 1) | $1.2 \times 10^3$ | $2.56 \times 10^4$ | $2.59 \times 10^4$ | $1.76 \times 10^4$ |
| germ-repellent plastic (A) | 0 | $5.99 \times 10^1$ | 0 | $2 \times 10^1$ |

As can be seen in Table 1, with *E. coli*, the germ-repellent plastic (A) of the present invention provides a 99.9% reduction in the swab test as compared to the comparative plastic (Control 1). In other words, the germ-repellent plastic (A) only has 0.11% of the adhesion of the comparative plastic (Control 1).

TABLE 2

EXAMPLE 1,

Sheet Sample with *S. aureus*

|  | Replicate 1 | Replicate 2 | Replicate 3 | Average |
|---|---|---|---|---|
| comparative plastic (Control 1) | $2.61 \times 10^4$ | $2.19 \times 10^4$ | $2.05 \times 10^4$ | $2.28 \times 10^4$ |
| germ-repellent plastic (A) | $3.2 \times 10^2$ | $4.4 \times 10^2$ | $1.2 \times 10^2$ | $2.9 \times 10^2$ |

As can be seen in Table 2, with *S. aureus*, the germ-repellent plastic (A) of the present invention provides a 98.7% reduction in the swab test as compared to the comparative plastic (Control 1). In other words, the germ-repellent plastic (A) only has 1.3% of the adhesion of the comparative plastic (Control 1).

Furthermore, a tube (without accelerated ageing) according to germ-repellent plastic A passed the ISO 10993-5 test. The melt flow index (according to ASTM D1238-10) for the germ-repellent plastic of Example C/D was 0.9 g/10 min, while the corresponding melt flow index for the POE blend (Control 1) was 0.88 g/10 min, which is only a +2.3% variance.

Example 2

A germ-repellent plastic (B) and a comparative plastic (Control 2) were prepared as in EXAMPLE 1, except that the twin-screw extruder temperature ranges from 110° C. in the front to 190° C. in the rear when preparing the masterbatch. The single-screw extruder temperature ranges from 210° C. in the front to 235° C. in the back when preparing the germ-repellent plastic. Furthermore, these samples were extruded from a single-screw extruder to form a length of tubing rather than the sheet of EXAMPLE 1.

A swab test (above) is conducted comparing germ-repellency of the germ-repellent plastic (B) with that of the comparative plastic (Control 2).

TABLE 1

EXAMPLE 2,

Tube Sample with *E. coli*

|  | Replicate 1 | Replicate 2 | Replicate 3 | Average |
|---|---|---|---|---|
| comparative plastic (Control 2) | $2.44 \times 10^3$ | $1.01 \times 10^4$ | $6.22 \times 10^3$ | $6.25 \times 10^3$ |
| germ-repellent plastic (B) | $3.60 \times 10^2$ | $3.20 \times 10^2$ | $1.43 \times 10^2$ | $2.74 \times 10^2$ |

As can be seen in Table 1, with *E. coli*, the germ-repellent plastic (B) of the present invention provides a 95.6% reduction in the swab test as compared to the comparative plastic (Control 2). In other words, the germ-repellent plastic (B) only has 4.4% of the adhesion of the comparative plastic (Control 2).

TABLE 2

EXAMPLE 2,

Tube Sample with *S. aureus*

|  | Replicate 1 | Replicate 2 | Replicate 3 | Average |
|---|---|---|---|---|
| comparative plastic (Control 2) | $1.21 \times 10^5$ | $1.70 \times 10^5$ | $1.15 \times 10^5$ | $1.35 \times 10^5$ |
| germ-repellent plastic (B) | $2.86 \times 10^4$ | $1.50 \times 10^4$ | $9.8 \times 10^3$ | $1.78 \times 10^4$ |

As can be seen in Table 2, with *S. aureus*, the germ-repellent plastic (B) of the present invention provides a 86.8% reduction in the swab test as compared to the comparative plastic (Control 2). In other words, the germ-repellent plastic (B) only has 13.2% of the adhesion of the comparative plastic (Control 2).

The test was continued and samples of the germ-repellent plastic (C, D) and the comparative plastic (Control 3, 4) are subjected to the swab test again after accelerated ageing of 22 and 43 days, respectively.

TABLE 3

EXAMPLE 2,

Tube Sample with *E. coli* (22 days ageing)

|  | Replicate 1 | Replicate 2 | Replicate 3 | Average |
|---|---|---|---|---|
| comparative plastic (Control 3) | $1.08 \times 10^4$ | $6.87 \times 10^3$ | $1.24 \times 10^3$ | $6.30 \times 10^3$ |
| germ-repellent plastic (C) | $2.05 \times 10^1$ | $1.42 \times 10^2$ | $1.02 \times 10^2$ | $8.82 \times 10^1$ |

TABLE 4

EXAMPLE 2,

Tube Sample with *E. coli* (43 days ageing)

|  | Replicate 1 | Replicate 2 | Replicate 3 | Average |
|---|---|---|---|---|
| comparative plastic (Control 4) | $5.48 \times 10^3$ | $2.46 \times 10^3$ | $1.32 \times 10^3$ | $3.09 \times 10^3$ |
| germ-repellent plastic (D) | $4.00 \times 10^1$ | $7.40 \times 10^1$ | $3.60 \times 10^2$ | $1.58 \times 10^2$ |

As can be seen in Tables 3-4, with *E. coli*, the germ-repellent plastic (C) of the present invention provides a 98.6% reduction in the swab test as compared to the comparative plastic (Control 3) when subjected to 22 days accelerated ageing, and the germ-repellent plastic (D) of the present invention provides a 94.9% reduction in the swab test as compared to the comparative plastic (Control 4) when subjected to 43 days accelerated ageing In other words, the germ-repellent plastic (C) only has 1.40% of the adhesion of the comparative plastic (Control 3) when subjected to 22 days accelerated ageing and the germ-repellent plastic (D) only has 5.12% of the adhesion of the comparative plastic (Control 4) when subjected to 43 days accelerated ageing. In other words, this shows that the current invention maintains significant *E. coli* germ-repellency even after accelerated ageing of 22 and 43 days.

TABLE 5

EXAMPLE 2,

Tube Sample with *S. aureus* (22 days ageing)

|  | Replicate 1 | Replicate 2 | Replicate 3 | Average |
|---|---|---|---|---|
| comparative plastic (Control 3) | $1.17 \times 10^5$ | $1.20 \times 10^5$ | $1.21 \times 10^5$ | $1.19 \times 10^5$ |
| germ-repellent plastic (C) | $1.93 \times 10^4$ | $1.62 \times 10^4$ | $1.94 \times 10^4$ | $1.83 \times 10^4$ |

TABLE 6

EXAMPLE 2,

Tube Sample with *S. aureus* (43 days ageing)

|  | Replicate 1 | Replicate 2 | Replicate 3 | Average |
|---|---|---|---|---|
| comparative plastic (Control 4) | $1.21 \times 10^5$ | $1.27 \times 10^5$ | $1.23 \times 10^5$ | $1.24 \times 10^5$ |
| germ-repellent plastic (D) | $1.18 \times 10^4$ | $8.99 \times 10^3$ | $6.90 \times 10^3$ | $9.23 \times 10^3$ |

As can be seen in Tables 5-6, with *S. aureus*, the germ-repellent plastic (C) of the present invention provides a 84.7% reduction in the swab test as compared to the comparative plastic (Control 3) when subjected to accelerated ageing for 22 days, and the germ-repellent plastic (D) of the present invention provides a 92.5% reduction in the swab test as compared to the comparative plastic (Control 4) when subjected to accelerated ageing for 43 days. In other words, the germ-repellent plastic (C) only has 15.3% of the adhesion of the comparative plastic (Control 3) when subjected to accelerated ageing for 22 days and the germ-repellent plastic (D) only has 7.46% of the adhesion of the comparative plastic (Control 4) when subjected to accelerated ageing for 43 days.

Example 3

The masterbatch is prepared according to EXAMPLE 1, except that no EVA is present. Instead, a mixture of 91% by weight of an ethylene/acrylic acid/maleic acid terpolymer intermediate plastic is comingled in a twin screw extruder with 9% by weight ceteareth anti-biofouling compound to form a masterbatch. The temperature at the front of the twin screw extruder is 110° C. and the temperature at the back is 200° C.

A basic plastic contains a blend of LDPE polymer and EVA polymer. The masterbatch and the basic plastic are comingled in a single-screw extruder to form germ-repellent plastic samples (E-G). Specifically, a single-screw extruder extrudes the germ-repellent plastic into tubes (E-G) as per EXAMPLES 2-3, except that the single-screw extruder has a temperature ranging from 180° C. in the front to 215° C. in the back.

Comparative plastic samples (Controls 5-7) containing only the basic plastic (LDPE/EVA blend) is also prepared in an identical manner, except that no masterbatch, intermediate plastic, or anti-biofouling compound is included.

A swab test (above) is conducted comparing germ-repellency of the germ-repellent plastic samples (E-G) with that of the comparative plastic samples (Controls 5-7).

TABLE 1

EXAMPLE 3,

Sheet sample with *E. coli*

|  | Replicate 1 | Replicate 2 | Average |
|---|---|---|---|
| comparative plastic (Control 5) | $2.27 \times 10^1$ | $2.25 \times 10^1$ | $2.26 \times 10^1$ |
| germ-repellent plastic (E) | 0 | 0 | 0 |

TABLE 2

EXAMPLE 3,

Tube sample with *E. coli* (22 days ageing)

|  | Replicate 1 | Replicate 2 | Average |
|---|---|---|---|
| comparative plastic (Control 6) | $7.6 \times 10^2$ | $4.6 \times 10^2$ | $6.1 \times 10^2$ |
| germ-repellent plastic (F) | $2.00 \times 10^1$ | $2.12 \times 10^1$ | $2.06 \times 10^1$ |

TABLE 3

EXAMPLE 3,

Tube sample with *E. coli* (45 days ageing)

|  | Replicate 1 | Replicate 2 | Average |
|---|---|---|---|
| comparative plastic (Control 7) | 0 | 0 | 0 |
| germ-repellent plastic (G) | 0 | 0 | 0 |

As can be seen in Tables 1-3, with *E. coli*, when formed as a tube, the germ-repellent plastic (E) of the present invention provides a >99% reduction in the swab test as compared to the comparative plastic (Control 5); the germ-repellency of the germ-repellent plastic (F) after 22 days accelerated ageing is 96.6% germ-repellency as compared to the comparative plastic (Control 6); and in the test of the germ-repellent plastic (G) after 45 days accelerated ageing, no bacteria stuck to either the sample (G) or the comparative plastic (Control 7).

TABLE 4

EXAMPLE 3,

Tube sample with *S. aureus*

|  | Replicate 1 | Replicate 2 | Average |
|---|---|---|---|
| comparative plastic (Control 5) | $2.25 \times 10^4$ | $3.04 \times 10^4$ | $2.65 \times 10^4$ |
| germ-repellent plastic (E) | $2.28 \times 10^2$ | $1.21 \times 10^2$ | $1.75 \times 10^2$ |

TABLE 5

EXAMPLE 3,

Tube sample with *S. aureus* (22 days ageing)

|  | Replicate 1 | Replicate 2 | Average |
|---|---|---|---|
| comparative plastic (Control 6) | $1.81 \times 10^4$ | $2.80 \times 10^4$ | $2.31 \times 10^4$ |
| germ-repellent plastic (F) | $1.36 \times 10^3$ | $2.56 \times 10^3$ | $1.96 \times 10^3$ |

TABLE 6

EXAMPLE 3,

Tube sample with *S. aureus* (45 days ageing)

|  | Replicate 1 | Replicate 2 | Replicate 3 | Average |
|---|---|---|---|---|
| comparative plastic (Control 7) | $2.24 \times 10^4$ | $3.98 \times 10^4$ | $8.87 \times 10^4$ | $5.03 \times 10^4$ |
| germ-repellent plastic (G) | $1.76 \times 10^3$ | $1.08 \times 10^3$ | $2.20 \times 10^3$ | $1.68 \times 10^3$ |

As can be seen in Tables 4-6, with *S. aureus*, when formed as tube, the germ-repellent plastic (E) of the present invention provides a 99.3% reduction in the swab test as compared to the comparative plastic (Control 5); the germ-repellent plastic (F) of the present invention provides a 91.5% reduction in the swab test as compared to the comparative plastic (Control 6) after 22 days of accelerated ageing; and the germ-repellent plastic (G) of the present invention provides a 96.7% reduction in the swab test as compared to the comparative plastic (Control 8) after 45 days of accelerated ageing.

Furthermore, the melt flow index of the germ-repellent plastic E is 2.30 g/10 min, as compared to the comparative plastic Control 5 which is 1.92 g/10 min, meaning that Plastic E is +20% with respect to Control 5. The melt flow index was tested according to ASTM D1238-10 under conditions of 190° C. and 2.16 kg.

Example 4

The masterbatch is prepared containing a mixture of 83.3% by weight EVA basic plastic is comingled in a twin-screw extruder with, 8.3% by weight ethylene/acrylic acid/maleic acid terpolymer intermediate plastic and 8.3% by weight ceteareth anti-biofouling compound. The twin-screw extruder has a temperature range from 110° C. in the front to 200° C. in the back.

A basic plastic contains a blend of PP and EVA. The masterbatch and the basic plastic are comingled to form germ-repellent plastic samples (H-K). Specifically, a single-screw extruder extrudes the germ-repellent plastic into tubes (H-K) as per EXAMPLES 2-3, except that the single-screw extruder has a temperature ranging from 190° C. in the front to 225° C. in the back. Furthermore, the basic plastic is comingled (via melt-extrusion) with the masterbatch at a weight ratio of 9:1.

Comparative plastic samples (Controls 8-11) containing only the basic plastic (PP/EVA blend) is also prepared in an identical manner, except that no masterbatch, intermediate plastic, or anti-biofouling compound is included.

A swab test (above) is conducted comparing germ-repellency of the germ-repellent plastic samples (H-K) with that of the comparative plastic samples (Controls 8-11).

TABLE 1

EXAMPLE 4,

Tube sample with *S. aureus*

|  | Replicate 1 | Replicate 2 | Average |
|---|---|---|---|
| comparative plastic (Control 8) | $1.67 \times 10^5$ | $1.51 \times 10^5$ | $1.59 \times 10^5$ |
| germ-repellent plastic (H) | $7.4 \times 10^3$ | $5.4 \times 10^3$ | $6.4 \times 10^3$ |

TABLE 2

EXAMPLE 4,

Tube sample with *S. aureus* (22 days ageing)

|  | Replicate 1 | Replicate 2 | Average |
|---|---|---|---|
| comparative plastic (Control 9) | $1.46 \times 10^3$ | $2.62 \times 10^3$ | $2.04 \times 10^3$ |
| germ-repellent plastic (I) | $4.0 \times 10^1$ | $7.02 \times 10^2$ | $3.71 \times 10^2$ |

TABLE 3

EXAMPLE 4,

Tube sample with *S. aureus* (62 days ageing)

|  | Replicate 1 | Replicate 2 | Average |
|---|---|---|---|
| comparative plastic (Control 10) | $4.67 \times 10^4$ | $1.35 \times 10^4$ | $3.01 \times 10^4$ |
| germ-repellent plastic (J) | $2.28 \times 10^3$ | $6.16 \times 10^3$ | $4.22 \times 10^3$ |

TABLE 4

EXAMPLE 4,

Tube sample with *S. aureus* (97 days ageing)

|  | Replicate 1 | Replicate 2 | Replicate 3 | Average |
|---|---|---|---|---|
| comparative plastic (Control 11) | $1.04 \times 10^5$ | $1.52 \times 10^5$ | $1.03 \times 10^5$ | $1.20 \times 10^5$ |
| germ-repellent plastic (K) | $2.11 \times 10^3$ | $1.30 \times 10^3$ | $1.82 \times 10^3$ | $1.74 \times 10^3$ |

As can be seen in Tables 1-3, with *S. aureus*, when formed as a tube, the germ-repellent plastic (H) of the present invention provides a 96% reduction in the swab test as compared to the comparative plastic (Control 8); after 22 days accelerated ageing, the germ-repellent plastic (I) of the present invention provides a 81.8% reduction in the swab test as compared to the comparative plastic (Control 9); after 62 days of accelerated ageing, the germ-repellent plastic (J) of the present invention provides a 86.0% reduction in the swab test as compared to the comparative plastic (Control 10); and after 97 days of accelerated ageing, the germ-repellent plastic (K) of the present invention provides a 98.4% reduction in the swab test as compared to the comparative plastic (Control 11).

While not shown, the germ-repellency with *E. coli* for the above germ-repellent plastics is from 97-100% when tested as above.

Furthermore, the melt flow index of the germ-repellent plastic H is 1.02 g/10 min, as compared to the comparative plastic Control 8 which is 0.90 g/10 min which indicates an increase of 13.3%. The melt flow index was tested according to ASTM D1238-10 under 230° C. and 2.16 kg. Furthermore, when Plastic H is tested vs. Control 8, Plastic H shows a decreased tensile strength (Type V, according to ASTM D638-10, at a speed of 5 mm/min) of 8.5%, a decreased elongation of 0.9%, and a decreased Young's modulus of 5.4%. Finally, the germ-repellent plastic H passed the ISO 10993-5 test and the ISO 10993-10 test.

Example 5

An anti-biofouling compound (poly(ethylene glycol) sorbitol hexaoleate is combined with a basic plastic formed of PVC at a weight ratio of 1:1000 in a single-screw extruder to form a germ-repellent plastic. The single-screw extruder has a temperature ranging from 90° C. in the front to 145° C. in the back. The single-screw extruder directly extrudes the germ-repellent plastic into a tube.

A swab test (above) is conducted comparing germ-repellency of the germ-repellent plastic samples (L-M) with that of the comparative plastic samples (Controls 11-12).

TABLE 1

EXAMPLE 5,

Tube sample with *E. coli*

|  | Replicate 1 | Replicate 2 | Replicate 3 | Average |
|---|---|---|---|---|
| comparative plastic (Control 11) | $4.14 \times 10^3$ | $2.25 \times 10^3$ | $1.66 \times 10^4$ | $7.66 \times 10^3$ |
| germ-repellent plastic (L) | 0 | 0 | $2.00 \times 10^1$ | $6.67 \times 10^0$ |

TABLE 2

EXAMPLE 5,

Tube sample with *E. coli* (22 days ageing)

|  | Replicate 1 | Replicate 2 | Replicate 3 | Average |
|---|---|---|---|---|
| comparative plastic (Control 12) | $3.36 \times 10^3$ | $1.50 \times 10^3$ | $2.32 \times 10^3$ | $2.39 \times 10^3$ |
| germ-repellent plastic (L) | $6.80 \times 10^2$ | $6.60 \times 10^2$ | $4.00 \times 10^1$ | $4.60 \times 10^2$ |

As can be seen in Tables 1-2, with *E. coli*, when formed as a tube, the germ-repellent plastic (K) of the present invention provides a >99.9% reduction in the swab test as compared to the comparative plastic (11); after accelerated ageing of 22 days, the germ-repellent plastic (L) of the present invention provides a 80.8% reduction in the swab test as compared to the comparative plastic (12).

TABLE 3

EXAMPLE 5,

Tube sample with S. aureus

|  | Replicate 1 | Replicate 2 | Replicate 3 | Average |
|---|---|---|---|---|
| comparative plastic (Control 12) | $9.69 \times 10^4$ | $7.73 \times 10^4$ | $6.48 \times 10^4$ | $7.97 \times 10^4$ |
| germ-repellent plastic (L) | $5.69 \times 10^3$ | $8.01 \times 10^3$ | $1.10 \times 10^4$ | $8.23 \times 10^3$ |

TABLE 4

EXAMPLE 5,

Tube sample with S. aureus (22 days ageing)

|  | Replicate 1 | Replicate 2 | Replicate 3 | Average |
|---|---|---|---|---|
| comparative plastic (Control 13) | $6.31 \times 10^3$ | $3.26 \times 10^3$ | $7.05 \times 10^3$ | $5.54 \times 10^3$ |
| germ-repellent plastic (M) | $6.40 \times 10^2$ | $2.81 \times 10^2$ | $1.20 \times 10^2$ | $3.47 \times 10^2$ |

As can be seen in Tables 3-4, with S. aureus, when formed as a tube, the germ-repellent plastic (L) of the present invention provides a 89.7% reduction in the swab test as compared to the comparative plastic (11); after accelerated ageing of 22 days, the germ-repellent plastic (M) of the present invention provides a 93.8% reduction in the swab test as compared to the comparative plastic (12).

When testing according to ASTM D638-10, Type V, at a speed of 10 mm/min was conducted, the germ-repellent plastic L shows a 6% increase in tensile strength, a 2.9% increase in elongation, and a 6.1% increase in Young's modulus.

Example 6

A masterbatch is formed in a twin-screw extruder by comingling 91% by weight of an ethylene/acrylic acid/maleic acid terpolymer intermediate plastic in the presence of 9% by weight of a ceteareth anti-biofouling compound. The temperature of the twin-screw extruder ranged from 110° C. I the front to 190° C. in the rear.

The basic plastic is a blend of two ethylene-octene POEs. The masterbatch is combined with the basic plastic at a weight ratio of 1:54. The masterbatch and the basic plastic are fed into a single-screw extruder having a temperature ranging from 210° C. in the front to 235° C. in the rear to form a germ-repellent plastic (N) and extrudes it directly into a tube. A comparative example (Control 13) is formed with the same blend of two ethylene-octene POEs, but with no masterbatch.

The swab test to compare germ-repellency is conducted on germ-repellent plastic N and results in a reduction of E. coli by 91% while the reduction of S. aureus is 85% compared to Control 13. Furthermore germ-repellent plastic N passes the ISO 10993-5 test.

Example 7

A masterbatch is formed according to EXAMPLE 6, except that the temperature of the twin-screw extruder ranges from 90° C. in the front to 190° C. in the back. A basic plastic contains a blend of PP and EVA. The weight ratio of basic plastic to masterbatch is 45:1 and the single-screw extruder temperature ranges from 150° C. in the front to 200° C. in the rear. The single-screw extruder forms a sheet of germ-repellent plastic (P) and a comparative example (Control 14). A second single-screw extruder forms the germ-repellent plastic (Q-R) directly into tubes and ranges in temperature form 190° C. in the front to 225° C. in the rear. Similar comparative examples (Control 15-16) with the same blend of PP and EVA, but no masterbatch are formed as well.

The swab test to compare germ-repellency is conducted on germ-repellent Plastic P and results in a reduction of E. coli by 99% while the reduction of S. aureus is 99% compared to Control 14. Germ-repellent plastic Q provides an E. coli reduction of 99% and a S. aureus reduction of 96% as compared to Control 15. After 22 days of accelerated ageing, germ-repellent plastic R provides an E. coli reduction of 99% and a S. aureus reduction of 97% as compared to Control 16.

Example 8

The masterbatch and germ-repellent plastics of EXAMPLE 7 are formed as described except that the temperature of the extruder ranges from 190° C. in the front to 210° C. in the back, and the germ-repellent plastic is injection moulded into a connector for use as a gas pathway of a respiratory device as Plastic S. A comparative example without the masterbatch is also formed as Control 17. When tested according to the swab test herein, Plastic S and results in a reduction of E. coli by 99% while the reduction of S. aureus is 97% compared to Control 17.

Example 9

The masterbatch and germ-repellent plastics of EXAMPLE 3 are formed as described except that the temperature throughout the extruder is 145° C. and the germ-repellent plastic is injection moulded into a connector for use as a gas pathway component of a respiratory device as Plastic T. A comparative example without the masterbatch is also formed as Control 18. When tested according to the swab test herein, Plastic T results in a reduction of E. coli by 99% while the reduction of S. aureus is 97% compared to Control 18.

It should be understood that the above only illustrates and describes examples whereby the present invention may be carried out, and that modifications and/or alterations may be made thereto without departing from the spirit of the invention.

It should also be understood that certain features of the invention, which are, for clarity, described in the context of separate embodiments, may also be provided in combination in a single embodiment. Conversely, various features of the invention which are, for brevity, described in the context of a single embodiment, may also be provided separately, or in any suitable subcombination.

The publications, references, etc. specifically cited herein are each hereby incorporated by reference in its entirety. However, no admission is made as to their availability and/or relevance as prior art, either alone or in combination.

What is claimed is:

1. A germ-repellent plastic for use in a gas pathway component of a respiratory device comprising:
   A) a masterbatch, comprising:
   A1) an anti-biofouling compound selected from the group consisting of a polyol, a polyether polyol, and a combination thereof; or wherein the anti-biofouling compound is selected from the group consisting of a polyether, a poly(ethylene glycol) ether, a polysorbate, and a combination thereof; or wherein the anti-biofouling compound is selected from the group consisting of poly(ethylene glycol) sorbitan monolaurate, poly(ethylene glycol) sorbitan monooleate, poly(ethylene glycol) sorbitol hexaoleate, ceteareth, and a combination thereof; and (A2) an intermediate plastic comprising a random terpolymer; the random terpolymer is a random terpolymer comprising a monomer selected from the group consisting of an ethylene monomer, an acrylic ester monomer, a maleic anhydride monomer and a combination thereof or a random terpolymer comprising an ethylene monomer, an acrylic ester monomer, and a maleic anhydride monomer; or a random terpolymer comprising a polymer backbone comprising ethylene monomers, acrylic ester monomers, and maleic anhydride monomers; and B) a basic plastic selected from the group consisting of a blend of a low-density polyethylene polymer and an ethyl vinyl acetate copolymer, a blend of a polypropylene polymer and an ethyl vinyl acetate copolymer, a blend of polyolefin elastomer polymers, and a polyvinyl chloride polymer.

2. The germ-repellent plastic according to claim 1, wherein the intermediate plastic does not contain the same polymeric segment as the basic plastic.

3. The germ-repellent plastic according to claim 1, wherein the masterbatch comprises from 0.001% by weight to 50% by weight; or from 0.001% by weight to 20% by weight; or from 0.01% by weight to 15% by weight, of the germ-repellent plastic.

4. The germ-repellent plastic according to claim 1, wherein the intermediate plastic comprises at least one polymeric segment that is compatible with the basic plastic.

5. The germ-repellent plastic according to claim 1, wherein the anti-biofouling compound comprises from 0.01% by weight to 25% by weight; or from 0.1% by weight to 20% by weight; or from 0.5% by weight to 15% by weight of the masterbatch.

6. The germ-repellent plastic according to claim 1, wherein the basic plastic is a polyvinyl chloride polymer and wherein the anti-biofouling compound and the polyvinyl chloride polymer are comingled to form the germ-repellent plastic.

7. The germ-repellent plastic according to claim 6, wherein the anti-biofouling compound comprises from 0.001% by weight to 50% by weight; or from 0.001% by weight to 20% by weight; or from 0.01% by weight to 15% by weight, of the germ-repellent plastic.

8. The germ-repellent plastic according to claim 6, wherein the basic plastic comprises from 50% by weight to 99.999% by weight; or from 80% by weight to 99.999% by weight; or from 85% by weight to 99.99% by weight, of the germ-repellent plastic.

9. The germ-repellent plastic according to claim 1, wherein the germ-repellent plastic possess a germ-repellency efficiency of at least 50%; or at least 75%; or at least 85%; or at least 90%; or at least 95%.

10. The germ-repellent plastic according to claim 1, wherein the germ-repellency has a shelf-life of greater than or equal to one year.

11. The germ-repellent plastic according to claim 1, wherein the germ-repellent plastic is biocompatible according to the ISO 10993 test, the ISO 18562 test, and a combination thereof.

12. The germ-repellent plastic according to claim 1, wherein the germ-repellent plastic comprises a physical property, wherein the basic plastic comprises the same physical property, and wherein the germ-repellent plastic's physical property differs from the basic plastic's same physical property by less than or equal to ±20%; or ±10%; or ±5%.

13. A method for manufacturing a germ-repellent plastic for use in a gas pathway of a respiratory device comprising the steps of:
    A) providing an anti-biofouling compound selected from the group consisting of a polyol, a polyether polyol, and a combination thereof; or wherein the anti-biofouling compound is selected from the group consisting of a polyether, a poly(ethylene glycol) ether, a polysorbate, and a combination thereof; or wherein the anti-biofouling compound is selected from the group consisting of polyethylene glycol sorbitan monolaurate, poly(ethylene glycol) sorbitan monooleate, poly(ethylene glycol) sorbitol hexaoleate, ceteareth, and a combination thereof;
    B) providing a basic plastic selected from the group consisting of a blend of a low-density polyethylene polymer and an ethyl vinyl acetate copolymer, a blend of a polypropylene polymer and an ethyl vinyl acetate copolymer, a blend of polyolefin elastomer polymers, and a polyvinyl chloride polymer; and
    C) providing an intermediate plastic; the intermediate plastic comprising a random terpolymer; or a random terpolymer comprising a monomer selected from the group consisting of an ethylene monomer, an acrylic ester monomer, a maleic anhydride monomer and a combination thereof; or a random terpolymer comprising an ethylene monomer, an acrylic ester monomer, and a maleic anhydride monomer; or a random terpolymer comprising a polymer backbone comprising ethylene monomers, acrylic ester monomers, and maleic anhydride monomers;
    D) comingling the anti-biofouling compound with an intermediate plastic to form a masterbatch; and
    E) comingling the masterbatch with the basic plastic to form the germ-repellent plastic.

14. The method according to claim 13, wherein the comingling step takes place in an extruder, a mould, and a combination thereof; or an extruder.

15. A gas pathway component of a respiratory device comprising the germ-repellent plastic according to claim 1.

16. A respiratory device comprising the gas pathway component of a respiratory device according to claim 15.

* * * * *